(12) United States Patent
Appling et al.

(10) Patent No.: US 8,317,773 B2
(45) Date of Patent: Nov. 27, 2012

(54) CATHETER WITH OPEN FACED SLOPED END PORTION

(75) Inventors: William M. Appling, Granville, NY (US); Theodore J. Beyer, Queensbury, NY (US); Carol L. Lancette, Hudson Falls, NY (US)

(73) Assignee: Angio Dynamics, Inc., Latham, NY (US)

( * ) Notice: Subject to any disclaimer, the term of this patent is extended or adjusted under 35 U.S.C. 154(b) by 695 days.

(21) Appl. No.: 11/557,369

(22) Filed: Nov. 7, 2006

(65) Prior Publication Data

US 2008/0108975 A1    May 8, 2008

(51) Int. Cl.
  *A61M 25/00* (2006.01)
  *A61M 31/00* (2006.01)
(52) U.S. Cl. ........................................ 604/530; 604/500
(58) Field of Classification Search .................. 604/27, 604/39, 43, 93, 158, 164, 264, 280, 283, 604/284
See application file for complete search history.

(56) References Cited

U.S. PATENT DOCUMENTS

| | | | |
|---|---|---|---|
| 4,134,402 A * | 1/1979 | Mahurkar | 604/44 |
| D272,651 S | 2/1984 | Mahurkar | |
| 4,568,329 A | 2/1986 | Mahurkar | |
| 4,601,697 A * | 7/1986 | Mammolenti et al. | 604/43 |
| 5,037,403 A * | 8/1991 | Garcia | 604/532 |
| 5,167,623 A * | 12/1992 | Cianci et al. | 604/43 |
| 5,209,723 A * | 5/1993 | Twardowski et al. | 604/43 |
| 5,222,966 A | 6/1993 | Perkins et al. | |
| 5,290,267 A | 3/1994 | Zimmermann | |
| 5,330,444 A | 7/1994 | Webler et al. | |
| 5,395,316 A | 3/1995 | Martin | |
| 5,405,320 A | 4/1995 | Twardowski et al. | |
| 5,441,510 A | 8/1995 | Simpson et al. | |
| 5,443,457 A | 8/1995 | Ginn et al. | |
| 5,451,216 A | 9/1995 | Quinn | |

(Continued)

FOREIGN PATENT DOCUMENTS

EP    0351206 B1    9/1994

(Continued)

OTHER PUBLICATIONS

Spire Biomedical, ALTA™ GOLD Fixed Tip: , http://www.spirecorp.com/spire-biomedical/catheters-and-devices/gold -series/ALTA-GOL....

(Continued)

*Primary Examiner* — Kevin C Sirmons
*Assistant Examiner* — William Carpenter
(74) *Attorney, Agent, or Firm* — Tara L. Clothier; Ryan D. Artis

(57) ABSTRACT

A vascular access catheter is disclosed that has a catheter shaft with a distal end portion with a distal tip having a sloped face that is positioned at an acute angle from the distal tip relative to a longitudinal axis of the catheter shaft. A first, second, and third lumen extend longitudinally through the catheter shaft. The third lumen is configured for receiving a guidewire and may extend a partial length of the catheter or substantially the entire length of the catheter. The first lumen has an aperture located in the angled edge distal end portion of the catheter next to the distal tip and communicates with the first lumen. The second lumen has an aperture that is positioned in the outer surface of the catheter shaft that is in communication with the second lumen, and is spaced proximally from the first lumen aperture.

5 Claims, 7 Drawing Sheets

U.S. PATENT DOCUMENTS

| | | | | |
|---|---|---|---|---|
| 5,571,093 | A | 11/1996 | Cruz et al. | |
| 5,603,991 | A * | 2/1997 | Kupiecki et al. | 427/508 |
| 5,681,336 | A | 10/1997 | Clement | |
| 5,685,867 | A | 11/1997 | Twardowski et al. | |
| 5,807,329 | A * | 9/1998 | Gelman | 604/102.03 |
| 5,827,229 | A * | 10/1998 | Auth et al. | 604/171 |
| 5,961,486 | A | 10/1999 | Twardowski et al. | |
| 6,004,310 | A | 12/1999 | Bardsley et al. | |
| 6,113,579 | A | 9/2000 | Eidenschink et al. | |
| 6,221,049 | B1 | 4/2001 | Selmon et al. | |
| 6,409,700 | B1 | 6/2002 | Siegel et al. | |
| 6,478,775 | B1 | 11/2002 | Galt et al. | |
| 6,482,169 | B1 * | 11/2002 | Kuhle | 604/6.16 |
| 6,485,481 | B1 | 11/2002 | Pfeiffer | |
| 6,786,884 | B1 | 9/2004 | DeCant, Jr. et al. | |
| 6,808,510 | B1 | 10/2004 | DiFiore | |
| 6,849,068 | B1 * | 2/2005 | Bagaoisan et al. | 604/523 |
| 6,869,417 | B1 | 3/2005 | Walters | |
| 6,872,192 | B2 | 3/2005 | Nash et al. | |
| 6,942,635 | B2 | 9/2005 | Rosenblatt et al. | |
| 6,979,318 | B1 | 12/2005 | McDonald et al. | |
| 6,997,894 | B2 * | 2/2006 | Caresio | 604/6.16 |
| 7,066,925 | B2 | 6/2006 | Gately | |
| RE39,451 | E * | 12/2006 | Kuhle | 604/6.16 |
| D540,467 | S | 4/2007 | Mori | |
| D541,936 | S | 5/2007 | Patterson | |
| D542,413 | S | 5/2007 | Mori | |
| 7,282,041 | B2 | 10/2007 | Igarashi et al. | |
| D581,529 | S | 11/2008 | Moehle | |
| 7,485,107 | B2 | 2/2009 | DiFiore et al. | |
| 2002/0026156 | A1 | 2/2002 | Quinn | |
| 2002/0032432 | A1 | 3/2002 | Nash et al. | |
| 2002/0065492 | A1 | 5/2002 | McGuckin, Jr. et al. | |
| 2002/0188167 | A1 * | 12/2002 | Viole et al. | 600/16 |
| 2003/0144623 | A1 * | 7/2003 | Heath et al. | 604/4.01 |
| 2004/0249337 | A1 * | 12/2004 | DiFiore | 604/40 |
| 2004/0249338 | A1 | 12/2004 | DeCant, Jr. et al. | |
| 2005/0033264 | A1 | 2/2005 | Redinger | |
| 2005/0197633 | A1 | 9/2005 | Schwartz | |
| 2006/0004316 | A1 | 1/2006 | DiFiore et al. | |
| 2006/0004325 | A1 * | 1/2006 | Hamatake et al. | 604/43 |
| 2006/0036218 | A1 | 2/2006 | Goodson, IV et al. | |
| 2006/0089618 | A1 | 4/2006 | McFerran et al. | |
| 2006/0100572 | A1 | 5/2006 | DiMatteo et al. | |
| 2006/0142703 | A1 | 6/2006 | Carter et al. | |
| 2006/0206055 | A1 | 9/2006 | Ice | |
| 2007/0060908 | A1 * | 3/2007 | Webster et al. | 604/509 |
| 2007/0066964 | A1 | 3/2007 | Atkins | |
| 2007/0078412 | A1 | 4/2007 | McGuckin, Jr. et al. | |
| 2007/0088328 | A1 | 4/2007 | Melsheimer | |
| 2007/0225661 | A1 * | 9/2007 | Ash et al. | 604/284 |
| 2008/0009784 | A1 | 1/2008 | Leedle | |
| 2008/0091104 | A1 | 4/2008 | Abraham | |
| 2008/0154217 | A1 | 6/2008 | Carrez et al. | |
| 2009/0182305 | A1 | 7/2009 | Tjelmeland | |

FOREIGN PATENT DOCUMENTS

| | | |
|---|---|---|
| WO | WO 99/38550 | 8/1999 |
| WO | 2005082442 A1 | 9/2005 |
| WO | 2007053741 A1 | 5/2007 |
| WO | WO 2009/051969 | 4/2009 |

OTHER PUBLICATIONS

U.S. Patent Application File History for Design U.S. Appl. No. 29/329,418.

U.S. Patent Application File History for co-pending U.S. Appl. No. 12/392,220 (US Published Application Serial No. 2009-0157051 A1).

U.S. Patent Application File History for co-pending U.S. Appl. No. 12/046,926 (US Published Application Serial No. US 2008/0154186 A1).

* cited by examiner

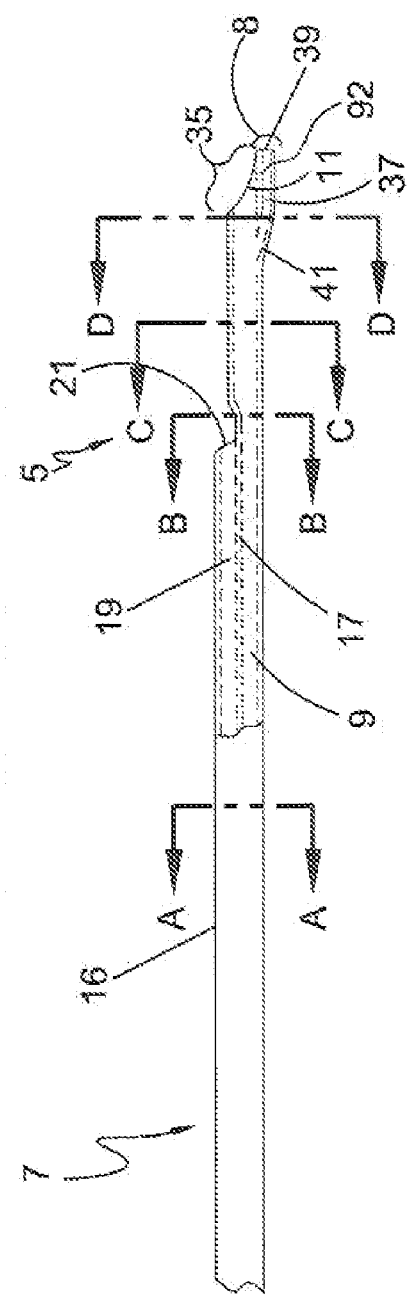
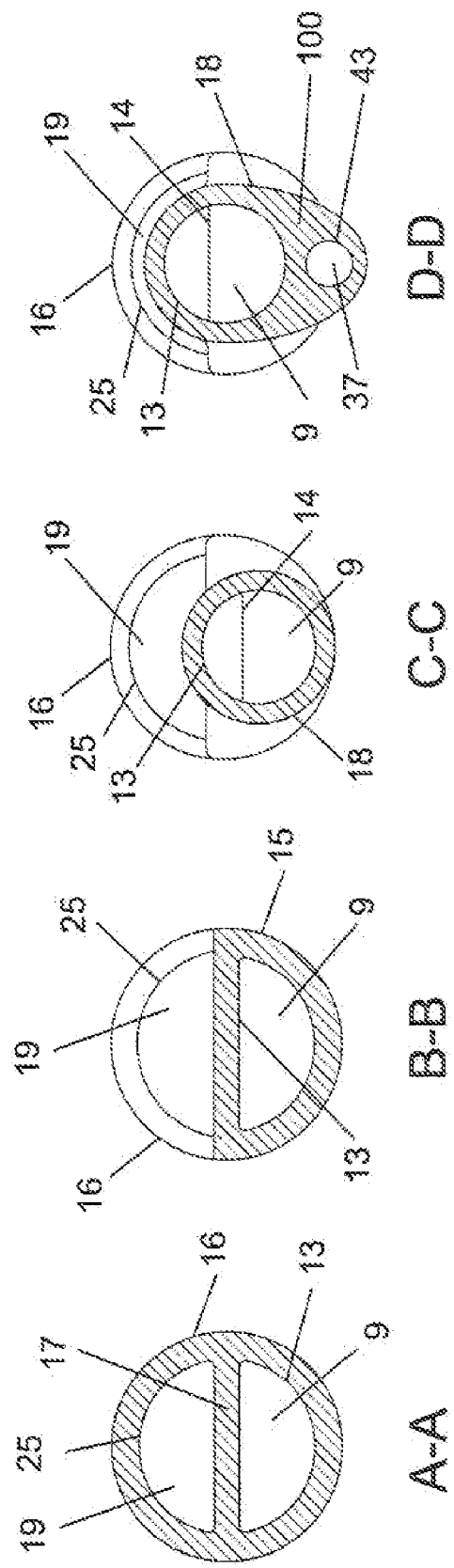
FIG. 2A
FIG. 2B

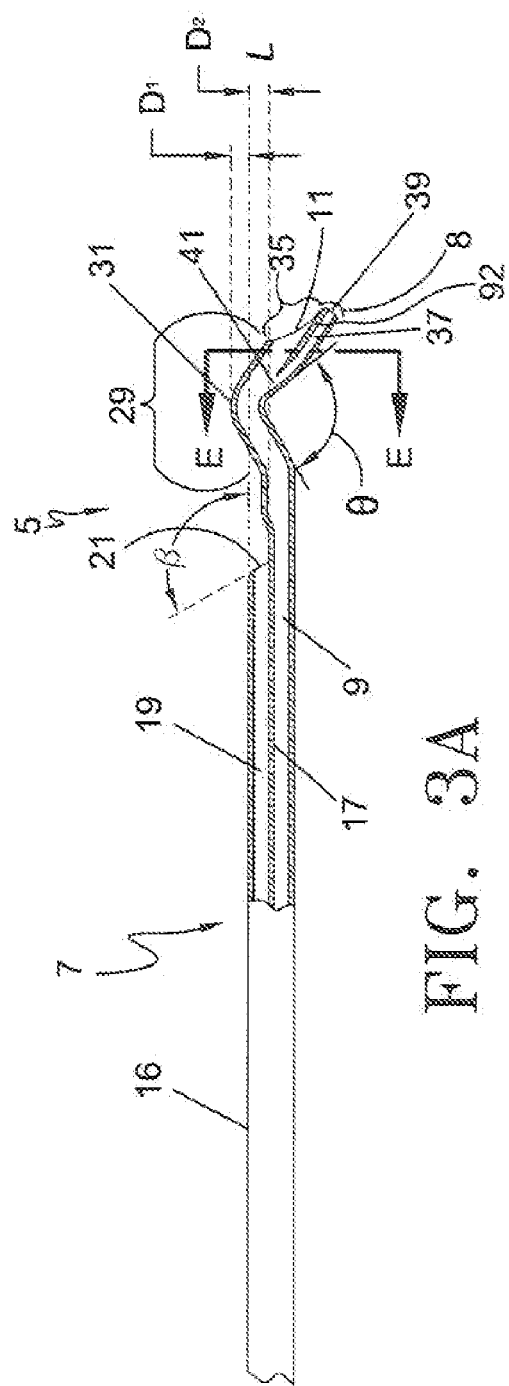
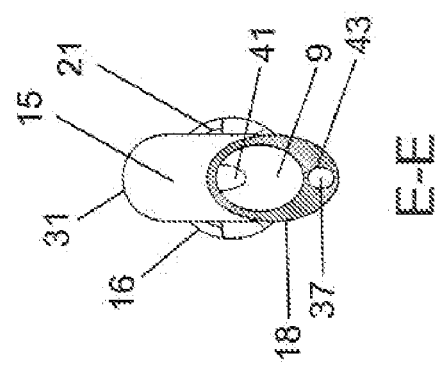
FIG. 3A
FIG. 3B

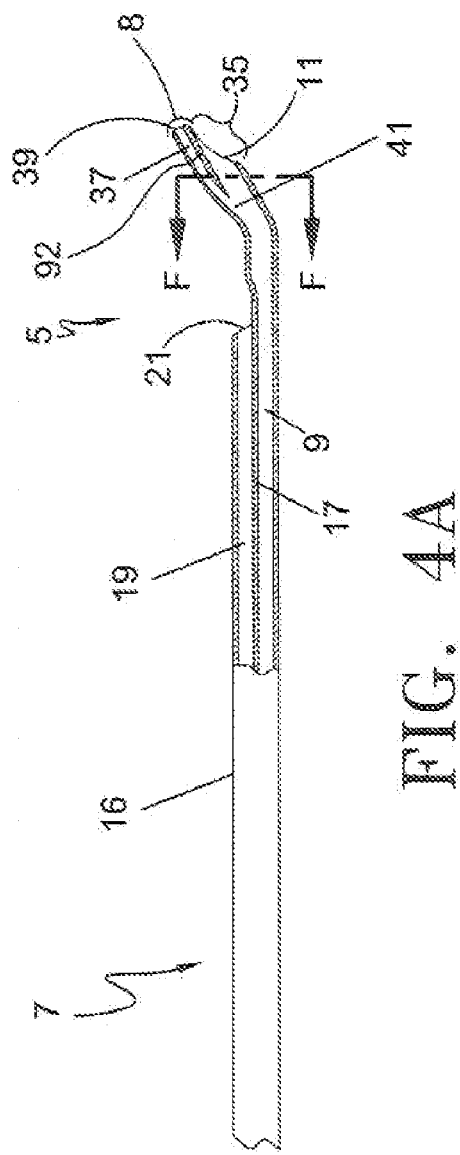
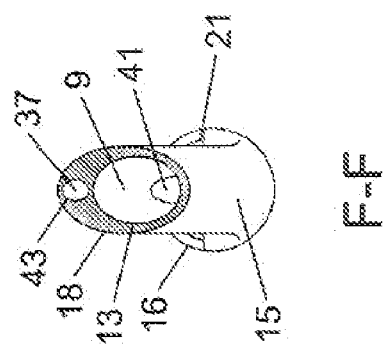
FIG. 4A
FIG. 4B

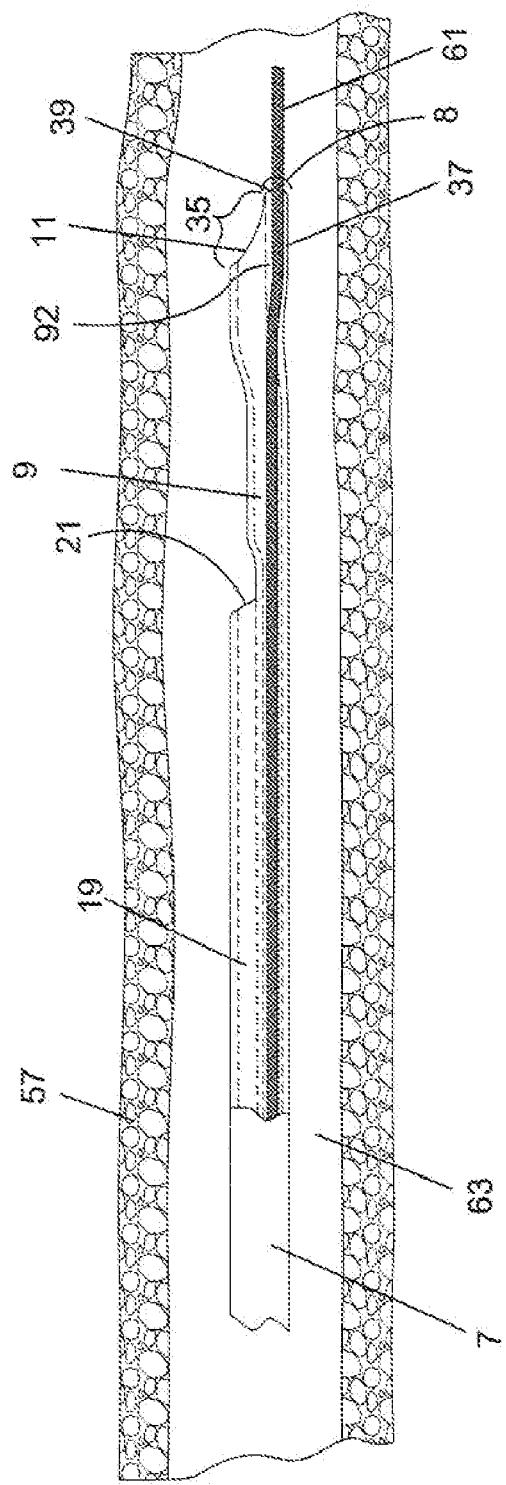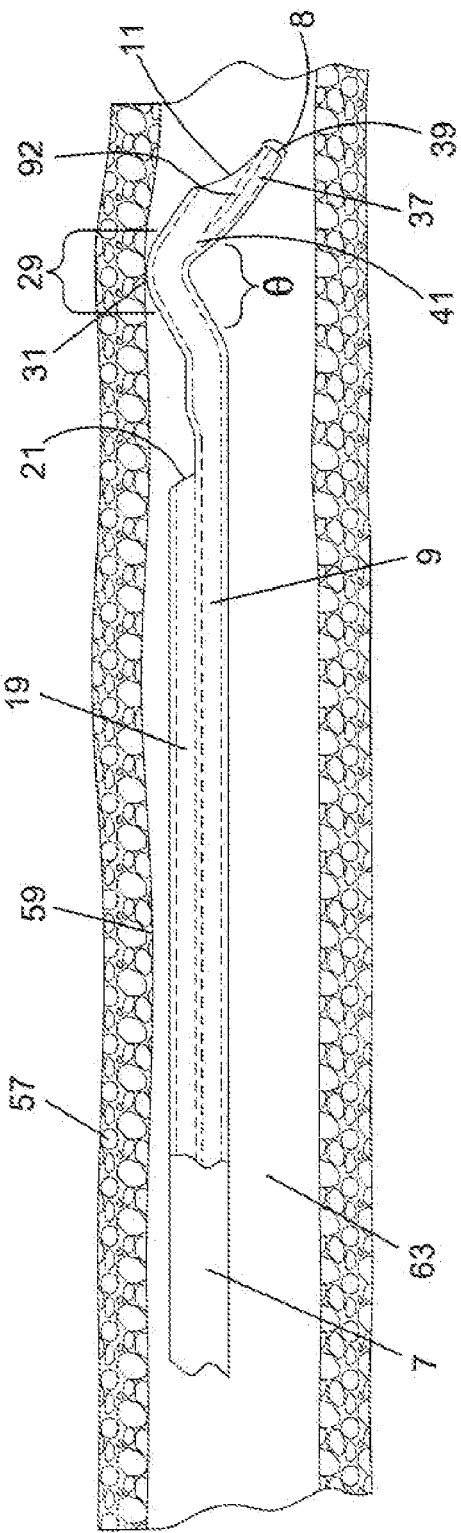
FIG. 5A
FIG. 5B

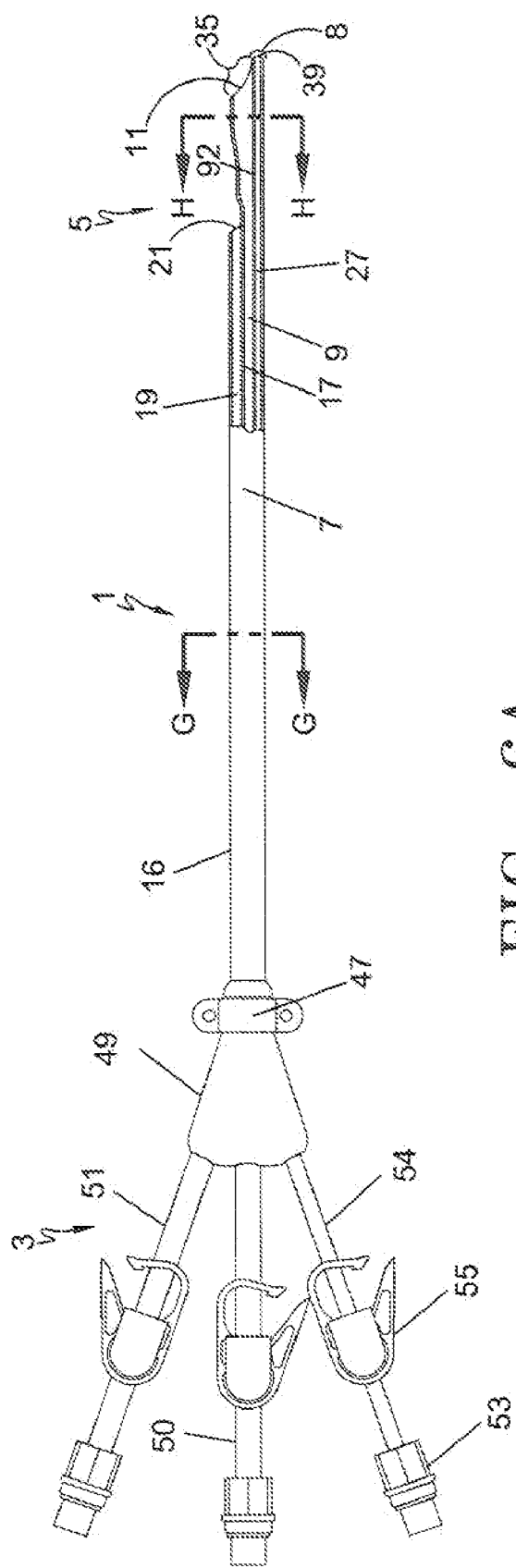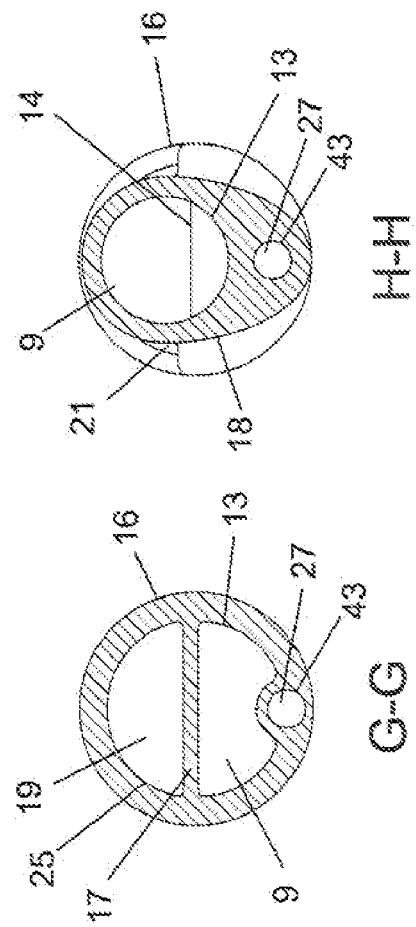
FIG. 6A
FIG. 6B

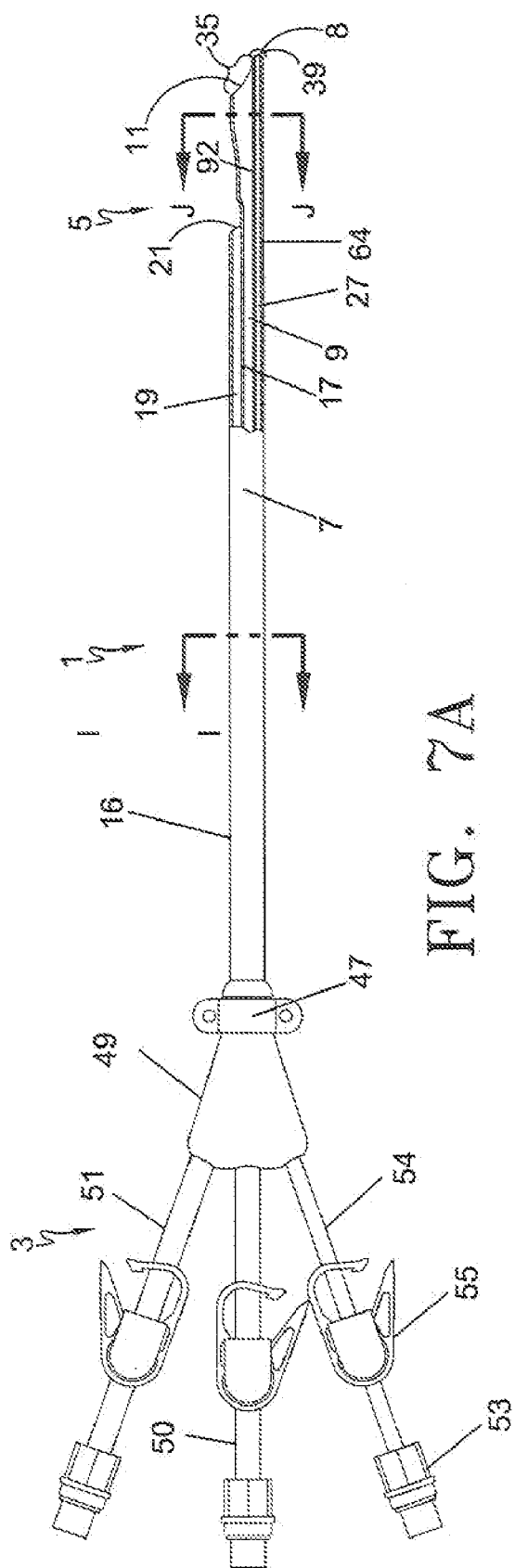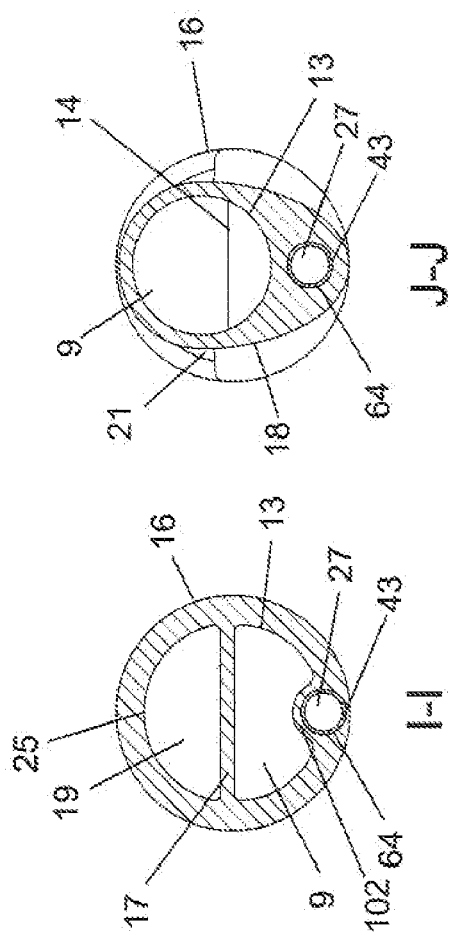
FIG. 7A
FIG. 7B

CATHETER WITH OPEN FACED SLOPED END PORTION

FIELD OF THE INVENTION

The present invention pertains to the field of medical devices. More particularly, the present invention relates to blood treatment catheters and a method of using such catheters.

BACKGROUND OF THE INVENTION

Hemodialysis is a method for removing waste products such as potassium and urea from the blood, such as in the case of renal failure. During hemodialysis, waste products that have accumulated in the blood because of kidney failure are transferred via mass transfer from the blood across a semi permeable dialysis membrane to a balanced salt solution. The efficiency of a hemodialysis procedure depends on the amount of blood brought into contact with the dialysis membrane. A flow of 250 milliliters of blood per minute under a pressure gradient of 100 millimeters of mercury is considered a minimum requirement for adequate dialysis. Over the past several years, flow rates between 350 milliliters per minute and 400 milliliters per minute have become common.

The long hours and the frequency of the dialysis treatment in patients with renal failure require reliable, continued access to the venous system for blood exchange. Long-term venous access mechanisms commonly used for hemodialysis treatment include vascular access ports, dialysis grafts, and hemodialysis catheters. One type of blood treatment catheter that is well-known in the art is a dual or triple-lumen hemodialysis catheter. These catheters are designed to provide long-term access to the venous system for dialysis. The dual-lumen catheter typically has an inflow lumen for withdrawing blood to be treated from a blood vessel and an outflow lumen for returning cleansed blood to the vessel. The distal segment of the catheter is typically positioned at the junction of the superior vena cava and right atrium to obtain a blood flow of sufficient volume to accommodate dialysis treatment requirements. This allows blood to be simultaneously withdrawn from one lumen, to flow into the dialysis circuit, and be returned via the other lumen. Triple lumen catheters function in a similar manner but have an additional smaller lumen which may be used for guidewire insertion, administration and withdrawal of fluids such as drugs or blood sampling, and for injection of contrast media required for imaging procedures.

To optimize blood flow rates during dialysis and reduce treatment times, catheters have been designed to maximize the cross-sectional lumen area of the inflow and outflow lumens. It is well known in the art that blood flow rates are negatively impacted if the cross-sectional area of the lumens does not remain essentially consistent and as large as possible throughout the entire length of the catheter from the proximal portion of the catheter to the distal portion of the catheter. Catheters with large, consistent luminal space typically have exit ports with blunt or flat-faced open tips, so as not to compromise the luminal area. Typically the exit port at the distal end of the catheter is cut at a 90 degree angle to the axis of the catheter.

While blunt, open ended catheters maintain optimal flow rates, they are difficult to insert into the patient because of their blunt leading ends. An introducer sheath will often be used to facilitate insertion. The introducer sheath has a dilating tip which is easily advanced through the track and into the vessel. The sheath has a large lumen into which the blunt-tipped catheter is inserted and advanced into the vessel. Although an introducer sheath may facilitate catheter placement, use of a sheath has several disadvantages. A sheath increases the risk of air embolism due to the presence of air gaps between the sheath and catheter. In addition, procedures that use an introducer sheath result in an enlarged insertion track due to the larger diameter of the sheath relative to the catheter. The use of a sheath also increases procedure time and costs.

A guidewire insertion technique is therefore often the preferred insertion technique for dialysis catheter placement. A guidewire is a thin, flexible wire that is usually made of stainless steel and has an atraumatic tip. A guidewire is typically inserted into a lumen of a dual or triple lumen catheter and then the catheter is advanced over the guidewire through the tissue track and into the vessel. The guidewire also provides additional stiffness or reinforcement in the wall of a catheter, to prevent kinking or accordianing of the catheter shaft as it is advanced through a tissue track and into a vessel.

If a guidewire is used for insertion of a blunt-end catheter with a large distal end opening, excess space will exist between the outer diameter of the guidewire and the inner diameter of the catheter lumen. A close fit between the lumen and the inserted guidewire is not dimensionally possible, thus leaving an annular gap between the guidewire and the distal opening of the catheter lumen. The excess annular space causes the leading distal edge of the catheter to accordion proximally over the guidewire during insertion, resulting in difficulties in advancing the catheter into the vessel. The distal portion of the catheter may grab or snare tissue as the practitioner attempts to advance the catheter into and through the vessel. This can increase procedure time, prevent the practitioner from reaching the intended target site within a patient vessel, or potentially cause other complications.

To overcome insertion difficulties common with inserting blunt tipped catheters, dialysis catheters have been designed with conical tapered distal portions that are narrower compared to the proximal portion of the catheter. The conical tip acts as a dilator to facilitate advancement of the catheter through the tissue track and into the vessel. These conical tip designs may include a guidewire lumen that exits from the distal tip of the catheter through a guidewire opening of reduced diameter, typically 0.037 inches.

While conical, tapered tip designs address the problems associated with inserting blunt tip full lumen distal end designs, they are disadvantageous in that they do not allow for optimum flow rates due to the reduced lumen diameter at the distal tip. To overcome reduced flow rates, conical, tapered tip catheters have been designed with distal side facing port or apertures cut through the catheter sidewall. The ports are located proximal to the conical tapered section and accordingly provide an exit channel from the lumen at a location where the cross-sectional area of the lumen has not been reduced.

Using side holes or apertures eliminates the problems of reduced flow rates but side-facing apertures are more likely to occlude than distally facing apertures. Those side holes located adjacent to the vessel wall are more likely to become blocked by the vessel wall, and are thus prone to clot-formation. In addition, the presence of side holes compromises the effectiveness of a fluid lock. A fluid lock, as known in the art, is used to prevent clot formation within the catheter between dialysis sessions. Typically, a heparin—saline fluid solution is infused into the full length of the catheter lumens. The fluid lock will only be effective up to the first proximal side hole, where the fluid will exit from the catheter and be replaced by blood. In the absence of the heparin-saline fluid solution, a portion of the lumen distal of the first side hole will become occluded by clot formation, complicating future dialysis sessions.

Another common complication of dialysis catheters is occlusion of the inflow and outflow apertures due to contact between the catheter and the vessel wall at the location of the apertures. During dialysis, negative pressure is generated within the inflow lumen in order to draw blood from the vessel through the lumen and into the dialysis machine. The suction created by the negative pressure may cause the catheter to move away from the center of the vessel and into contact with the vessel wall. The vessel wall essentially blocks the aperture, preventing further blood from being drawn into the inflow lumen. Although not as, common, the outflow apertures may also come to rest up against the vessel wall, resulting in occlusion.

Thus, there exists a need in the art for a dual or triple lumen hemodialysis catheter that has a dilating distal tip that is not reduced in lumen cross-sectional area compared to the rest of the lumen. Such a lumen would be able to maintain consistent and optimal blood flow rats throughout the entire length of the catheter, eliminating the need for side hole ports. The catheter would have one lumen capable of receiving a guidewire that can provide enhanced guidewire tracking along various lengths of the catheter, thereby eliminating the need for an introducer sheath. The catheter would be designed to prevent occlusion of the blood lumen apertures by having a distal end shape that creates a barrier between the blood lumens and vessel wall.

A vascular access catheter has not yet been proposed that solves all of the above-mentioned problems. The vascular access catheter described herein addresses problems with prior art catheters by providing a hemodialysis catheter that has at least two lumens, each with at least one aperture, and a distal portion that has one lumen with a substantially open sloped face distal end portion with a distal tip and consistent cross-sectional area compared to the rest of the lumen of the catheter, which allows for maximum blood flow. The catheter also has a third lumen located adjacent the distal tip that is capable of receiving a guidewire. The guidewire aperture and the sloped face of the distal end portion facilitate insertion, without the use of an introducer sheath. The luminal cross-section area is maintained for the entire length of the catheter, eliminating the need for side holes, and thereby avoiding problems associated with compromised fluid lock and resulting side hole occlusion. The catheter may optionally include a curved or bent distal end shape to prevent contact between the lumen apertures and the vessel wall.

Accordingly, provided herein, in one aspect, is a hemodialysis catheter that may have two or three lumens and a sloped open-faced distal end portion that provides for optimal blood flow rats by maintaining a uniform cross-sectional area throughout the lumen, eliminating the need for attachments or additional steps, thereby minimizing procedure time and improving patient treatment outcomes.

A further purpose is to provide a catheter that maintains the cross-sectional area of the blood lumen of the catheter without increasing the outer diameter of the catheter.

A further purpose is to provide a transitional guidewire lumen that is positioned at the distal most edge of the sloped distal end portion of the catheter that does not cause the overall outer diameter of the catheter to be increased.

A further purpose is to provide a catheter that is capable of receiving a guidewire in a third lumen that is designed for optimal guidewire tracking without requiring the use of an introducer sheath. The lumen may extend a partial length of the catheter, where it may be joined to another lumen, or it may extend substantially all the way through to the proximal end of the catheter, which may be useful for injections or infusion of drug treatments.

A further purpose is to provide a catheter that minimizes occlusion of the lumen apertures of the catheter by providing a substantially curved distal portion that abuts against the vessel wall while the catheter is deployed in a vessel. The abutting curved distal portion acts to guard one of the lumen apertures of the catheter from being occluded, which in turn, maintains maximum blood flow.

A further purpose is to provide a catheter that has a distal portion that allows for increased ease of insertion of the catheter into a vessel. The insertion is facilitated by straightening the distal portion of the catheter from a substantially curved to a straight configuration, which causes less resistance upon insertion. The distal portion of the catheter is more flexible, compared to the rest of the catheter, which helps to facilitate straightening of the distal portion. The flexibility of the distal portion of the catheter allows the distal portion to return to its original configuration after the guidewire is removed.

It is a further purpose to provide a catheter that maximizes flow rates without requiring side hole ports.

It is yet another purpose to provide a non-conical distal end portion catheter that may be placed without the use of an introducer sheath.

Various other objectives and advantages will become apparent to those skilled in the art as more detailed description is set forth below. Without limiting the scope of the invention, a summary of some of the claimed embodiments of the invention is set forth below. Additional details of the summarized embodiments of the invention and/or additional embodiments may be found in the Detailed Description.

SUMMARY

A vascular access catheter is disclosed that has a catheter shaft with a distal portion that has a distal end portion with a distal tip having an angled, leading edge that is positioned at an acute angle from the distal tip relative to a longitudinal axis of the catheter shaft. A first, second, and third lumen extend longitudinally through the catheter shaft. The third lumen is configured for receiving a guidewire. The first lumen has an aperture located in the angled edge distal end portion of the catheter next to the distal tip and communicates with the first lumen. The second lumen has an aperture that is positioned in the outer surface of the catheter shaft that is in communication with the second lumen, and is spaced proximally from the first lumen aperture.

A method of inserting a vascular access catheter is also provided. The method involves providing the vascular access catheter described herein, inserting the catheter into a vessel in a patient body over the guidewire, positioning the distal portion of the catheter at a desired location within the vessel, and removing the guidewire from the third lumen.

BRIEF DESCRIPTION OF THE SEVERAL VIEWS OF THE DRAWINGS

The foregoing advantages and features, as well as other advantages and features, will become apparent with reference to the description and accompanying figures below, which are included to provide an understanding of the invention and constitute a part of the specification, in which like numerals represent like elements, and in which:

FIG. 2A is an enlarged partial cross-sectional view of the distal portion of the catheter of FIG. 1.

FIG. 2B illustrates three different cross-sectional views of the catheter shaft and one cross-sectional end view of the catheter of FIG. 2A along lines A-A, B-B, C-C, and D-D, respectively.

FIG. 3A is an enlarged partial cross-sectional view of an additional embodiment of the catheter with a curved distal portion.

FIG. 38 is a cross-sectional end view of the curved distal portion of the catheter of FIG. 3A.

FIG. 4A is a partial cross-sectional view of an additional embodiment of the catheter with a curved distal portion.

FIG. 4B is a cross-sectional end view of the curved distal portion of the catheter of FIG. 4A.

FIG. 5A is a partial cross-sectional side view of the catheter of FIGS. 3A and 38, while deployed inside a vessel with a guidewire inserted into the catheter.

FIG. 5B is a partial cross-sectional side view of the catheter of FIG. 5A after the guidewire has been removed from the catheter.

FIG. 6A is a plan view of a triple lumen catheter and a partial cross-sectional view of the distal portion.

FIG. 6B illustrates two different cross-sectional views of the catheter shaft of FIG. 6A, along lines G-G and H-H, respectively.

FIG. 7A is a plan view of an additional embodiment of a triple lumen catheter and a partial cross-sectional view of the distal portion.

FIG. 7B illustrates two different cross-sectional views of the catheter of FIG. 7A at the catheter shaft, along lines I-I and J-J, respectively.

DETAILED DESCRIPTION

Figure 1:
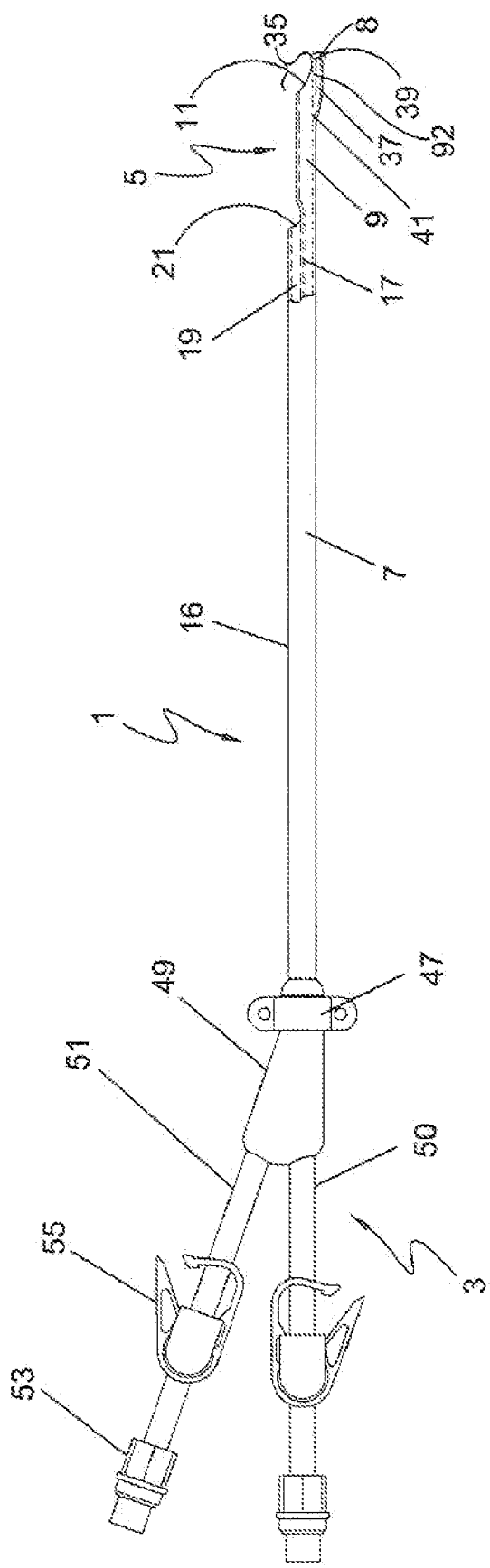
FIG. 1 is a plan view of the catheter and a partial cross-sectional view of the distal portion of the catheter.

The following detailed description should be read with reference to the drawings, in which like elements in different drawings are identically numbered. The drawings, which are not necessarily to scale, depict several embodiments and are not intended to limit the scope of the invention. The detailed description illustrates by way of example, not by way of limitation, the principles of the invention.

In various embodiments, and referring to FIGS. 1-7B, presented herein is an exemplary vascular access catheter, such as a hemodialysis catheter, and a method of inserting the catheter into the body of a patient.

FIG. 1 illustrates one embodiment of the hemodialysis catheter. In one aspect, the unitary catheter 1 has a proximal portion 3 and a distal portion 5. In this exemplary aspect, the distal portion 5 of the catheter 1 is substantially straight. In another aspect, the proximal portion 3 of the catheter 1 can be comprised of a bifurcate 49, a suture ring 47 coaxially arranged around the distal portion of the bifurcate 49, a suture ring 47 coaxially arranged around the distal portion of the bifurcate 49, a pair of extension tubes 50, 51, extension tube clamps 55, and catheter hub connectors 53 for connection to a dialysis machine. In this aspect, the catheter shaft 7 extends from the bifurcate 49 to the distal tip 8 at the distal portion 5 of the catheter 1. In one aspect, as illustrated in FIG. 1, in the unstressed configuration, the shaft 1 is positioned in a single plane.

In one aspect, the catheter shaft 7 can be comprised of an outer wall 16 and at least a first lumen 9 and second lumen 19 extending longitudinally through substantially the entire length of the catheter shaft 7. Lumen 19 is fluidly connected with extension tube 51, and lumen 9 is fluidly connected with extension tube 50. Both extension tubes 50, 51 communicate through bifurcate 49. In one example, blood can be withdrawn from the vessel of the patient into lumen 19 where it is passed through the extension tube 51 into the dialysis machine. Blood can be returned to the patient through extension tube 50 into lumen 9, which exits through the distal aperture 11 into the vessel of the patient.

In one example, the outer diameter of the catheter 1 is approximately 0.203 inches, although, as one skilled in the art will appreciate, other diameter catheters are within the scope of this invention. In another example, and not meant to be limiting, the usable length of the catheter shaft 7, as measured from the distal end of bifurcate 49 to the distal tip 8, is between approximately 20 cm to 55 cm, depending on the patient's anatomy and physician preference. In one aspect the catheter shaft 7 usable length is between approximately 32 and 36 cm.

In one aspect, the catheter 1 is a unitary catheter composed of carbothane, but any suitable material may be used, such as, but not limited to, polyurethane or silicone. In another aspect, the catheter 1 may also contain a radiopaque material to enhance visibility under fluoroscopy. At least a portion of the catheter shaft 7 forms the distal portion 5 of the catheter 1. In a further aspect, the catheter shaft 7 can be configured such that the shaft 7 is more flexible at its distal portion 5 than its proximal portion 3. In one example, and not meant to be limiting, the distal portion 5 can have a reduced diameter and be formed with less material, compared to the proximal portion 3 of the catheter shaft 7, such that the distal portion 5 is relatively more flexible than the proximal portion 3. The increased relative flexibility of the distal portion 5 allows the distal portion 5 of the catheter to be more easily advanced through the vessel. The catheter shaft 7 may optionally be comprised of materials of different durometers to produce a shaft 7 with enhanced flexibility at the distal portion 5. In various other aspects, the catheter shaft 7 can be configured to be stiffer at the proximal portion 3 outside of the patient's body for durability and more flexible at the distal portion 5 to facilitate insertion of the catheter 1 and to provide a catheter 1 with an atraumatic tip, when placed within a vessel of the patient.

In one additional aspect, the catheter 1 can have an inflow lumen 19 that is in fluid communication with an inflow aperture 21 that is defined in the exterior surface of the catheter 7 in the distal portion 5 of the catheter. The inflow lumen aperture 21 is in fluid communication with the second lumen 19 and is spaced proximally of the outflow lumen aperture 11. The inflow lumen 19 can be exemplarily used for withdrawal of blood from the patient. In one exemplary aspect, and as shown in FIG. 3A, the inflow aperture 21 can be sloped such that the cross-section of the inflow aperture 21 is forward-facing, and is positioned at an angle β greater than about 90 degrees relative to a longitudinal axis of the catheter shaft 7 (shown as line "L" in FIG. 3A). In another aspect, the catheter 1 has an outflow lumen 9 that can be exemplarily used for delivering cleansed blood back into the patient's circulatory system. In this example, blood exits the distal portion 5 of the catheter 1 through outflow aperture 11 that is defined in at least a portion of the distal end portion 35 that has a sloped face, distally of the inflow aperture 21, adjacent the distal tip 8 and in communication with the first lumen 9, as illustrated in FIGS. 1-7B. In yet another aspect, the two lumens 9 and 19 have inner walls 25 and 13, respectively, and are separated along their longitudinal length by, and share a common internal septum 17, illustrated along line A-A in FIG. 2B. One skilled in the art will appreciate that, although designated herein as inflow and outflow lumens, dialysis may be performed by reversing the blood flow through the lumens.

Hence, the terms first lumen and second lumen may also be used herein to designate the interchangeability of the outflow and inflow lumens, respectively. In one aspect, the inflow lumen can have a D-shaped lumen configuration, and the outflow lumen 9 can have a partially D-shaped lumen configuration, as illustrated in FIGS. 2A-7B. Of course, it is contemplated that the lumens of the catheter 1 may have any suitable cross-sectional lumen shape as required for the particular use of the catheter 1.

In one aspect, the catheter 1 can have a third guidewire lumen 37 that is defined at least in the region of the distal portion 5 of the catheter 1 and has an inner wall 43. The guidewire lumen 37 extends proximally from aperture 39 defined therein the distal most portion of the sloped face of the distal end portion 35 of the catheter, distal of the first aperture 11, to aperture 41, defined therein the distal portion 5 of the catheter 1, where lumen 37 is joined to and terminates within outflow lumen 9. In one example, the third lumen 37 can have a generally smaller transverse cross-sectional area than lumens 19 and 9, as illustrated, for example, in FIGS. 4B, 6B, and 7B. In this aspect, the guidewire lumen 37 is configured for slidably receiving at least a portion of a guidewire (not shown). The guidewire lumen 37 provides a guidewire track for the guidewire to facilitate insertion of the catheter 1 through tissue into the target vessel and allows for improved guidewire insertion and tracking techniques, as described above. In one aspect, the guidewire lumen 37 extends a partial length d the catheter 1. In one exemplary aspect, and not meant to be limiting, the length of the guidewire lumen 37 may be between approximately 3 mm and 10 mm, preferably. In another aspect, the length of the guidewire lumen 37 may be between approximately 6 mm and 7 mm in length. In one exemplary aspect, the inner diameter of guidewire lumen 37 may be approximately 0.037 inches so as to accommodate a guidewire with an outer diameter of approximately 0.035 inches, such that it is positioned in close surrounding relationship to at least a portion of an inserted guidewire, as illustrated in FIG. 5A. It is contemplated that other dimensions may be used for the third lumen 37 and the guidewire. These dimensions allow the guidewire to be slidably received within the lumen 37, while minimizing space between the outer diameter of the guidewire and the inner diameter of the lumen 37. In one aspect, the third lumen 37 can be centered below the outflow lumen 9, as illustrated in FIGS. 2B, 4B, 6B, and 7B, such that the luminal cross sectional area of the outflow lumen 9 is not compromised. In this aspect, the distal aperture 39 of the third lumen 37 is defined in the distal portion 5 and is positioned distal to the outflow lumen aperture 11 at the distal most portion of the sloped face, such that the distal aperture faces distally away from the catheter shaft and is angled proximally away from the distal tip, as exemplarily illustrated in FIGS. 1 through 7B.

In one aspect, the distal tip 8, outflow aperture 11, and the guidewire exit aperture 39 define a sloped distal end portion 35 of the distal portion 5 of the catheter 1 in which at least a portion of the distal end portion 35 is sloped with a sloped open face, as illustrated in FIGS. 1 through 7B. "Sloped", as it pertains to the description herein, means that at least a portion of the distal end portion 35 has an angled edge that is not at a perpendicular angle relative to the longitudinal axis of the catheter 1, and could exemplarily include end portions 35 defined by flat, arcuate, or extended arcuate surfaces. In one aspect, the angled edge is angled proximally away from the distal tip 8 and is positioned at an acute angle γ relative to a longitudinal axis of the catheter shaft 7, illustrated in FIG. 5A. In one aspect, the sloped distal end portion 35 is positioned at approximately 30 degrees relative to the longitudinal axis of the catheter 1. In this aspect, the sloped distal end portion 35 that extends from the proximal most edge of the outflow lumen aperture 11 to the distal most edge of the third lumen 37 is approximately 5 mm, although the length will vary based on the angle of the slope. The acute angle γ of the sloped angled edge of at least a portion of the distal end portion 35 may between approximately 15 degrees and 75 degrees relative to the longitudinal axis of the catheter shaft 7. In another exemplary aspect, the sloped distal end portion 35 is approximately 30 degrees relative to the longitudinal axis of the catheter shaft 7.

In another exemplary aspect, the sloped distal end portion 35 can be configured to act as a dilator to provide enhanced insertion and tracking functionality without compromising flow rates, as will be explained in greater detail below.

The distal portion 5, defined herein as the length between the distal most edge of the inflow aperture 21 and the distal most edge of the guidewire exit aperture 39, can, in one non-limiting example, be approximately 2.5 cm, and in the depicted embodiment in FIG. 1, be substantially straight. In this example, the length between the distal most edge of the inflow aperture 21 and the proximal most edge of the outflow lumen aperture 11 is approximately 2 cm, which provides sufficient separation between the respective outflow and inflow two lumens 9, 19 to minimize re-circulation of blood during dialysis. As one skilled in the art will appreciate, recirculation is a complication of dialysis in which treated blood exiting from the outflow aperture 11 is pulled back into the catheter 1 through the inflow aperture 21 and re-processed by the dialysis machine. Recirculation reduces the efficiency of the cleansing process and results in inadequate dialysis if recirculation rates are too high. By spacing the inflow aperture 21 and outflow aperture 11 sufficiently apart, the recirculation rate during treatment is reduced to an acceptable level.

FIG. 2A illustrates an enlarged sectional view of the distal portion 5 of the catheter shaft 7 of FIG. 1. The outer wall 16 of the proximal portion 3 of the catheter shaft 7 surrounds an outflow lumen 9 and an inflow lumen 19, which are separated by a common internal septum 17. In one aspect, the outflow lumen 9 extends from the proximal most end of the catheter shaft 7 to aperture 11, defined therein sloped distal end portion 35. In one aspect, inflow lumen 19 extends distally from the proximal most end of catheter shaft 7 to inflow aperture 21.

In one aspect, the distal portion 5 of the catheter 1 includes a sloped distal end portion 35, which is comprised of distal tip 8, guidewire exit aperture 39, and outflow lumen aperture 11. The sloped profile of distal end portion 35 performs several functions. The forward-facing slope provides a tapered leading edge to facilitate insertion and advancement of the catheter 1. The forward-facing orientation of the slope is angled away from the vessel wall to minimize engagement with the vessel wall, once inserted. The distal-most leading edge of the sloped end portion 35 terminates in a guidewire exit aperture 39 for optimized guidewire tracking. Distal end portion 35 also includes a forward-facing, full size outflow lumen 11. Thus, in one aspect, the sloped distal end portion 35 combines the features of a distal end profile capable of tracking over a guidewire and dilating the insertion track as well as minimizing vessel wall contact with an aperture that is not reduced in cross-sectional area.

In one aspect, the partial transitional guidewire lumen 37 that is adapted for insertion of a guidewire (not shown), allows for ease of insertion of the guidewire into the catheter 1 and also allows ease of insertion of the catheter 1 into a vessel over the guidewire. The guidewire lumen 37 has an inner diameter of approximately 0.037 inches, which closely fits around an inserted guidewire of approximately 0.035 inches. These dimensions allow the guidewire to slide within the lumen 37, while eliminating space between the outer diameter of the guidewire and the inner diameter of the lumen 37. This enhanced guidewire tracking prevents tissue from being snagged during advancement of the catheter 1 into a target location, and the distal end portion 35 provides a dilating function, thereby reducing trauma and tissue disruption to the vessel. The guidewire and catheter 1 may therefore be easily inserted into a vessel without requiring the use of an introducer sheath. One skilled in the art will appreciate that the elimination of the introducer sheath reduces procedure time and costs, and minimizes the risk of air embolism due to absence of air gaps between the sheath and the catheter 1.

In another aspect, the transitional partial guidewire lumen 37 provides enhanced guidewire tracking, such that the outer diameter of the catheter 1 does not have to be increased to accommodate the partial lumen 37 adjacent to the outflow lumen aperture 11 at the distal most edge of the distal tip 8. This allows the effective cross-sectional area of the outflow lumen 9 to be maintained to be substantially uniform throughout the catheter 1 and provides for maximum blood flow.

In one aspect, FIG. 2B illustrates four different cross-sectional views of the catheter shaft 7 of one exemplary embodiment. The lumen configuration of the catheter 1 transitions from a double-D lumen, illustrated along line A-A, to a single-D lumen, illustrated along line B-B, to a single round outflow lumen 9 illustrated along line C-C, finally ending in a single round outflow lumen 9 at the distal most tip of the catheter 1, with a guidewire lumen 37 located adjacent the outflow lumen 9, which is illustrated along line D-D.

The first cross-sectional view, A-A, illustrates the double-D lumen configuration of the catheter shaft 7 which extends to just proximal of line B-B, where the inflow lumen 19 terminates at aperture 21. In one aspect, the lumens of the catheter 1 have a double-D configuration. In another aspect, the catheter 1 may have any suitable cross-sectional lumen shape as required for the particular use of the catheter 1. The advantage of a double-D lumen configuration is that it allows for maximal flow rates for a catheter 1 circular in cross-sectional profile, which fact is well known in the art. The outflow lumen 9 and the inflow lumen 19 are shown separated by a common internal septum 17. The outflow lumen 9 has an inner wall 13. The inflow lumen 19 has an inner wall 25. As illustrated in line A-A, the common internal septum 17 has a width of approximately 0.144 inches. In this exemplary embodiment, each double-D lumen may have a height of approximately 0.064 inches.

A cross-sectional view of line B-B in the distal portion 5 of the catheter 1 is also illustrated. Outer wall 16 and inner wall 25 define the inflow lumen 19, which is shown as an end view, terminating proximally of line B-B. The outflow lumen 9 extends distally of the inflow lumen 19, which terminates at inflow aperture 21, proximal to line B-B. At the termination point of inflow aperture 21, the double-D lumen also terminates and is continued as a single-D lumen 9.

At line C-C, the single-D shaped lumen has transitioned to a single round shaped outflow lumen 9. In this view, the transitional wall 14 represents the inner wall of the common internal septum 17 of the outflow lumen 9 at the double-D lumen section. At line C-C, the outflow lumen 9 has an inner diameter of approximately 0.095 inches and an outer diameter of approximately 0.140 inches. The rounded outer profile of the catheter shaft 7 at line C-C is of a smaller outer cross-sectional diameter than the cross-sectional diameter of the catheter shaft 7 at line B-B, which measures 0.203 inches. The reduced diameter facilitates insertion and advancement of the distal end of the catheter 1 through the tissue track and into the vessel.

A cross-sectional end view of the catheter 1, as taken along line D-D, is also illustrated. The cross-sectional end view, taken along lines D-D of FIG. 2B illustrates the guidewire lumen 37. Lumen 37 has a substantially circular shape defined by an inner wall 43. The inner diameter of the guidewire lumen 37 is approximately 0.037 inches. The guidewire lumen 37 is capable of receiving a guidewire that is approximately 0.035 inches.

In this aspect, lumen 37 is surrounded by an expanded guidewire wall segment 100 that separates lumen 37 from outflow lumen 9. Wall segment 100 may be formed using several techniques well known in the art including re-forming existing shaft material, or using a supplemental tip-forming or a molding process. In one aspect, lumen 37 can be positioned within guidewire wall segment 100 to ensure that the cross-sectional area of outflow lumen 9 at the sloped distal end portion 35 is substantially equivalent to the cross-sectional area of the proximal portion 3 of the lumen 9.

In one aspect, although the profiles of the lumens 19 and 9 of the catheter 1 change at different sections of the catheter 1, the transverse cross-sectional lumen areas are maintained throughout the length of the catheter 1. Specifically, the cross-sectional area of each of the double-D lumens, taken along line A-A, which is approximately 0.00702 inches$^2$, is substantially equal to the cross-sectional area of the catheter 1 taken along line D-D, which is approximately 0.00708 inches$^2$. This substantially equivalent cross-sectional area allows for optimal and consistent blood flow within the catheter 1 throughout treatment of the patient.

In addition, unlike current unitary catheter designs, the catheter 1 allows for insertion over a guidewire utilizing a leading distal end guidewire aperture without increasing the overall diameter of the catheter 1 and without compromising the cross-sectional luminal area of the outflow lumen 9. In one aspect, the cross-sectional diameter of the sloped distal portion 35 taken along the axis of the catheter shaft 7 is 0.160 inches, but may range from 0.150 to 0.180 inches. The reduced cross-sectional diameter of the outflow lumen 9 at line D-D, which is approximately 0.043 inches less than the proximal portion 3 of the catheter shaft 7, which has a cross-sectional diameter of approximately 0.203 inches, which thus facilitates insertion and advancement of the catheter 1 into a patient's body without compromising the cross-sectional luminal area of the outflow lumen 9.

Accordingly, in one aspect, a catheter 1 with a non-conical sloped dilating distal portion 35 is provided that maintains a consistent, uniform luminal area throughout the entire length of the catheter shaft 7. The substantially completely open sloped face geometry of the outflow lumen aperture 11 of the distal tip 8 allows for maximum blood flow because the cross-sectional area of the outflow lumen 9 is maintained from the proximal portion 3 to the distal portion 5 of the catheter 1, while the outer diameter of the catheter 1 is not increased. Because of its size and orientation, the outflow lumen aperture 11 is not likely to occlude, compared with typical conical-tapered or blunt tip catheters with smaller side wall lumen openings.

FIG. 3A illustrates another embodiment of the catheter 1. In this embodiment, the catheter shaft 7 has a double-D lumen configuration at its proximal portion 3, which transitions to a circular configuration with inflow and outflow apertures, similar to the embodiment illustrated in FIG. 1. The catheter shaft 7 of FIG. 3A is different from FIG. 1 in that it has a substantially curved distal portion 5 instead of a straight distal portion 5 in an unstressed state. The distal portion 5 of catheter shaft 7 may have any suitable curved shape configuration, including, but not limited to a curved, bent or semi-helical shape.

As further distinguished from the first embodiment of catheter 1 illustrated in FIGS. 1 and 2, at least a portion of the distal portion 5 of the catheter 1 that is substantially curved, as illustrated in FIGS. 1-7B, is defined by a guard portion 29. In this aspect, the guard portion 29 has an apex 31 that is located at the outermost point of the guard portion 29. As illustrated in FIG. 3A, in one aspect, the apex is positioned distally of the second lumen aperture 21. In yet another aspect, a portion of the guard portion 29 is spaced from the longitudinal axis of the catheter shaft 7 a distance D1 that is equal to or greater than the distance D2 that the outer wall 16 of the inflow aperture 21 is spaced from the longitudinal axis of the catheter shaft 7, as also illustrated in FIGS. 3A and 3B. The substantially curved distal portion 5 acts to guard lumen aperture 21 of the catheter 1 from being occluded, which in turn, maintains maximum blood flow, as described above. The guard portion 29 is also defined by an inner angle θ opposite the apex 31. In various aspects, it is contemplated that when the catheter shaft 7 is in the unstressed state, the inner angle θ of at least a portion of the distal portion 5 of the catheter may be between approximately 45 degrees and 135 degrees. In another aspect, the inner angle θ can be equal to or greater than about 90 degrees, depending on the curvature of the guard portion 29. In yet another aspect, the inner angle θ can be approximately 90 degrees. Optionally, the curved distal portion 5 may have substantially straight portions on either side of the inner angle θ, or the curved distal portion 5 may be a substantially continuous series of arcuate arcs.

In one aspect, FIG. 3B illustrates the distal portion 5 of the catheter 1 of FIG. 3A along line E-E. As illustrated along line E-E of FIG. 3B, in one aspect, the apex 31 of the guard portion 29 can be configured so that, from a front elevational view, the distal end of the inflow aperture 21 is partially visible, being protected by portions of the apex 31 of the guard portion 29. The outer wall of the distal portion 5 of the catheter 1 transitions into a shared outer wall 18 of the outflow lumen 9 and the guidewire lumen 37, which has an inside wall 43. At least a portion of third lumen 37 and at least a portion of first lumen 41 are divided by and share a common wall 92. At least a portion of wall 92 is angled away from the longitudinal axis L of the catheter shaft along at least a portion of the length of the catheter shaft. In one aspect, at least a portion of the common internal wall 92 can be positioned on one side of the longitudinal axis L of the catheter shaft along at least a portion of the length of the catheter shaft.

In a further aspect, as shown in FIG. 3B, the space between the apex 31 and the outer wall 16 of the inflow aperture 21 can be configured to function as a guard to prevent aperture 21 from moving up against the vessel wall and at least partially or fully occluding the inflow aperture 21. In this aspect, as described above, the height D1 of apex 31 in relation to the longitudinal axis of catheter shaft 7 can be configured to be equal to or greater than the height D2 of the outer wall 16 of inflow aperture 21 in relation to the longitudinal axis of the catheter shaft 7, which should allow for the guard functionality. Thus, when the negative pressure of blood drawn into the inflow lumen 19 causes the catheter 1 to move toward the vessel wall, the apex 31 of the guard 29, rather than the inflow aperture 21, will abut up against the vessel wall.

In this aspect, the difference in height between the apex 31 of the guard portion 29 and the proximal most portion of the inflow aperture 21 helps the guard portion 29 to act as a guard to prevent inflow aperture 21 from contacting or resting against the vessel wall. The exemplified configuration of the guard portion 29 thus functions to ensure that aperture 21 remains positioned away from the vessel wall so as to avoid being partially or completely blocked and compromising outcome of the treatment session. As shown in the figures, apex 31, with its extended height, provides a separating barrier between the inflow aperture 21 and the outflow aperture 11, which acts to further minimize mixing cleansed and uncleansed blood during a dialysis session and decreases recirculation problems.

In another aspect, the guidewire lumen 37 shared outer wall 18, combined with the forward-facing orientation of the sloped distal end portion 35 also protects the outflow aperture 11 from being blocked if the catheter 1 comes into contact with the vessel wall. Referring to FIG. 3A, the catheter shaft 7 may be oriented such that it abuts the vessel wall at distal tip 8 rather than at apex 31. In this orientation, the distal tip 8 with guidewire exit aperture 39 contacts with the vessel wall and provides a spacing function similar to the guard 29 to protect the outflow aperture 11 from contacting and being blocked by the vessel wall. In this exemplified aspect, the forward-facing angle of the sloped distal end portion 35 is angled or oriented away from the vessel wall such that, as illustrated in FIG. 3A in the unstressed configuration, the shaft is positioned in a single plane, and the outflow aperture 11 will not become occluded by the vessel wall because it is protected by the distal tip 8.

In one aspect, as illustrated in FIG. 4A, catheter shaft 7 of can have a substantially bent distal portion 5 of the catheter 1 that defines an angle of greater than about 90 degrees relative to the longitudinal axis of the catheter shaft 7, such that the distal tip 8 is greater in height than the proximal most edge of the inflow lumen aperture 21. The clinical features described above in relation to the embodiment of the distal portion 5 of the catheter 1 illustrated in FIGS. 3A and 3B also apply to the embodiment illustrated in FIGS. 4A and 4B. In a further aspect, the embodiment illustrated in FIG. 4 provides a more direct blood flow path through lumen 9 which may enhance flow rates during dialysis.

A method of inserting the catheter 1 into a blood vessel is also disclosed herein and illustrated in FIGS. 54 and 5B. Although FIGS. 5A and 5B illustrate use of the catheter 1 embodied in FIGS. 3A and 3B, the method of inserting the catheter 1 may encompass the use of any of the embodiments of the catheter 1 described herein and illustrated in FIGS. 1 through 7. The method involves providing the catheter 1 described in any of FIGS. 1 through 7, inserting at least a portion of guidewire 61 into a vessel 57 in a patient body; inserting the proximal end of the guidewire 61 into the guidewire exit aperture 39 of the guidewire lumen 37; advancing the guidewire 61 through the guidewire lumen 37 and into the outflow lumen 9; inserting the catheter 1 into a vessel 57 in a patient body over the guidewire 61; positioning the distal portion of the catheter at a desired location within the target vessel 57; and removing the guidewire 61 from the catheter. If the catheter 1 of the embodiments illustrated in any of FIG. 3 or 4 is used, the method may further involve providing a catheter with a substantially curved or bent distal portion 5. The method may further involve straightening the distal portion of the catheter upon insertion of the guidewire 61 into the guidewire lumen 37. After the guidewire 61 is inserted into the guidewire lumen 37, the entire inserted guidewire 61 and the distal portion of the catheter become approximately parallel with the axis of the catheter shaft 7, as illustrated in FIG. 5A.

FIG. 5A illustrates the tapered profile of sloped distal end portion 35 with its leading distal tip 8. This profile provides an atraumatic dilating function by gradually expanding the tissue track from the approximate size of a guidewire, typically 0.035 inches, to the slightly larger diameter of the distal tip 8, to the diameter of the catheter shaft 7 at the proximal most edge of outflow aperture 11, which is approximately 0.160 inches, to the maximum diameter of the catheter shaft 7 at inflow aperture 21, which is approximately 0.203 inches. Because of the dilating profile of the catheter 1, use of an introducer sheath is not necessary.

FIG. 5B illustrates a partial sectional side view of the catheter of FIG. 5A deployed within a vessel 57 inside of a patient body after the guidewire 61 has been removed from the catheter shaft 7. When the guidewire 61 is removed from the catheter shaft 7, the distal portion of the catheter 1 then recovers to its substantially curved configuration. In one aspect, the distal portion 5 of the catheter 1 has flexibility and a shaped memory, formed during the manufacturing process of the catheter, and is configured to allow the distal portion 5 of the catheter 1 to be substantially straightened when the guidewire 61 is inserted into and advanced through the third lumen 27/37, as illustrated FIG. 5A. This also allows the substantially curved distal portion 5 of the catheter 1 to recover toward its original curved unstressed state after the guidewire 61 is removed from the third lumen 27/37. Thus, the inner angle θ of the guard portion 29 recovers to an angle equal to or greater than about 90 degrees from the catheter shaft 7 axis.

In one aspect, when the catheter 1 is deployed in the vessel 57, the catheter 1 may migrate from the center of the vessel lumen 63 and abut up against the inner wall 59 of the vessel 57, as shown in FIG. 5B. The guard 29 contacts the inner vessel wall 59 at apex 31. The apex 31 of the guard portion 29 acts as a shield, preventing the aperture 21 from being occluded by vessel wall 59. It also provides a recirculation barrier between the inflow aperture 21 and the outflow aperture 11.

Also shown in FIG. 5B, the guard 29 also acts to orient outflow aperture 11 more centrally within the vessel 57 where blood volume is highest, thereby further minimizing recirculation rates, increasing the efficiency of the dialysis session, and reducing vessel wall 59 trauma caused by sustained contact with the catheter.

FIG. 6A illustrates yet another embodiment of the catheter 1 at line G-G. In this embodiment, the catheter 1 is identical to the embodiment illustrated in FIG. 1, except that the catheter 1 has a guidewire lumen 27 which extends substantially the entire length of the catheter 1 from the distal tip 8 to bifurcate 49, where the guidewire 27 lumen is fluidly connected with extension tube 54.

FIG. 6B illustrates the cross-sectional area of the catheter 1 of FIG. 6A taken along line G-G and H-H. The cross-sectional view along line G-G illustrates the outflow lumen 9 and the inflow lumen 19 separated by a common internal septum 17 and a guidewire lumen 27 defined by an outer wall 43. The outer diameter of the catheter 1 is approximately 0.203 inches, equivalent to previous embodiments. In a further aspect, to accommodate the guidewire lumen 27 within the partial double-D section of the catheter 1 without increasing the outer diameter of the catheter 1, the common internal septum 17 can be positioned slightly off-center. This allows the effective cross-sectional area of each lumen 19 and 9 to be substantially equalized, and aids in providing substantially equalized flow rates in both the inflow and outflow directions. In one non-limiting example, the resulting cross-sectional area of each lumen 19 and 9 is approximately 0.0065 inches$^2$, which is approximately 0.0005$^2$ inches less than the transitional guidewire lumen embodiments previously illustrated. This luminal area reduction of 0.0005$^2$ is insignificant in terms of impact on flow rates. Thus, in this aspect, the cross-sectional luminal areas of the catheter 1 are maintained without having to increase the outer diameter of the catheter, as described above.

Along line H-H at the distal portion 5 of the catheter 1, the double-D lumen has transitioned to a single round outflow lumen 9. Also illustrated along line H-H, the cross-sectional lumen area of outflow lumen 9 is maintained at its largest diameter to distal aperture 11, as with the previous embodiments.

In one exemplary embodiment, illustrated in FIGS. 6A and 6B, it is contemplated that the guidewire lumen 27, which is fluidly connected with extension tube 54, may be used for the delivery of drugs, injections of fluids, such as contrast media, and for blood sampling, eliminating the need for the practitioner to place a secondary vascular access device. In addition, the cross-sectional luminal areas of previous embodiments are maintained without having to increase the outer diameter of the catheter 1. The substantially straight shape of the catheter 1 provides for direct blood flow paths and optimal flow rates in addition to minimal guidewire friction in comparison to curved embodiments. The continuous guidewire lumen 27 allows for the guidewire exchange or re-insertion, if necessary, after the catheter 1 has been placed in a vessel. The distal portion 5 of the catheter 1 is concentrically aligned within the outer circumference of the proximal portion 3 of the catheter shaft 7, as best illustrated in FIG. 6B, along line H-H. This alignment provides a structural barrier separating the inflow and outflow lumens 19 and 9, thereby minimizing recirculation rates during the dialysis session.

In one aspect as illustrated in FIGS. 7A and 7B, the guidewire lumen 27 may have a liner 64 placed along at least a portion of the inner wall 43 of the lumen 27. The liner 64 is a tubular structure that functions to increase the burst pressure of the guidewire lumen 27. Burst pressure is defined herein as the amount of pressure that the lumen 27 may withstand during high pressure applications, such as contrast media injections, before rupturing. The liner 64 allows a higher burst pressure of the lumen 27 by providing a liner 64 material with a higher yield stress than the material of the catheter shaft 7. The liner 64 may be made of any suitable material that may increase the burst pressure of the lumen 27, such as, but not limited to nylon or polyamide. The liner 64 may also reduce friction over the guidewire 61, thereby further enhancing guidewire 61 tracking capabilities of the lumen 27.

The liner 64 may have a wall thickness of between approximately 0.002 and 0.005 inches. The liner 64 may optionally be constructed of a higher strength material than the catheter shaft 7, so as to allow thinner surrounding catheter wall sections 102, thereby minimizing reduction in luminal cross-sectional area of the inflow 19 and outflow 9 lumens. The liner 64 disclosed herein may also be placed inside of the partial guidewire lumen 37 described herein in the previous embodiments and illustrated in FIGS. 1 through 5.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein, which equivalent are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the selected embodiments of the invention. Those skilled in the art may recognize other equivalents to the specific embodiments described herein which equivalents are intended to be encompassed by the claims attached hereto.

What is claimed is:

1. A method of inserting a vascular access catheter into a vessel, wherein the method comprises:
   a. providing a vascular access catheter, wherein the catheter comprises:
   a catheter shaft, wherein at least a portion of the catheter shaft forms a distal portion of the catheter, and wherein the distal portion has a distal end portion having a distal tip, wherein at least a portion of the distal end portion is substantially sloped with a sloped face that is angled proximally away from the distal tip and is positioned at an acute angle relative to a longitudinal axis of the catheter shaft; and
   a plurality of longitudinally extending lumens defined therein the catheter shaft, wherein the plurality of lumens comprises a first lumen, a second lumen, and a third lumen defined within the catheter shaft, wherein the first and second lumens extend substantially the entire length of the catheter shaft, wherein the third lumen is configured to selectively receive at least a portion of a guidewire, wherein at least a portion of the third lumen and at least a portion of the first lumen share a common wall, and wherein at least a portion of the common wall is angled away from the longitudinal axis such that in the unstressed configuration, the shaft is positioned in a single common plane, wherein the single common plane bisects the first, second, and third lumens and passes through the longitudinal axis of the catheter shaft, wherein the second lumen is positioned above the first lumen within the single common plane, and wherein the third lumen is positioned below the first lumen within the single common plane;
   a first lumen aperture defined in at least a portion of the distal end portion that has a sloped face, adjacent the distal tip and in fluid communication with the first lumen; and
   a second lumen aperture defined therein the exterior surface of the catheter shaft and in fluid communication with the second lumen, wherein the second lumen aperture is spaced proximally from the first lumen aperture, and
   a distal aperture defined in at least a portion of the distal end portion and in fluid communication with the third lumen, wherein the distal aperture faces distally away from the catheter shaft and is angled proximally away from the distal tip, wherein the distal portion of the catheter is substantially curved in an unstressed state and forms a guard portion having an apex that extends upwardly relative to the single common plane and defines an inner angle measured in the single common plane opposite the apex, wherein the apex is positioned distally of the second lumen aperture; and
   b. inserting the guidewire into a vessel in a patient body; and
   c. inserting a guidewire into the distal aperture of the third lumen; and
   d. advancing the guidewire through the third lumen and into the first lumen; and
   e. inserting the catheter into a vessel in a patient body over the guidewire; and
   f. positioning the distal portion of the catheter at a desired location; and
   g. removing the guidewire from the third lumen.

2. A vascular access catheter comprising:
   a catheter shaft, wherein at least a portion of the catheter shaft forms a distal portion of the catheter, and wherein the distal portion has a distal end portion having a distal tip, wherein at least a portion of the distal end portion is substantially sloped with a sloped face that is angled proximally away from the distal tip and is positioned at an acute angle relative to a longitudinal axis of the catheter shaft; and
   a plurality of longitudinally extending lumens defined therein the catheter shaft, wherein the plurality of lumens comprises a first lumen, a second lumen, and a third lumen defined within the catheter shaft, wherein the first and second lumens extend substantially the entire length of the catheter shaft, wherein the third lumen is configured to selectively receive at least a portion of a guidewire, wherein at least a portion of the third lumen and at least a portion of the first lumen share a common wall, and wherein at least a portion of the common wall is angled away from the longitudinal axis such that in the unstressed configuration, the shaft is positioned in a single common plane, wherein the single common plane bisects the first, second, and third lumens and passes through the longitudinal axis of the catheter shaft, wherein the second lumen is positioned above the first lumen within the single common plane, and wherein the third lumen is positioned below the first lumen within the single common plane;
   a first lumen aperture defined in at least a portion of the distal end portion that has a sloped face, adjacent the distal tip and in fluid communication with the first lumen; and
   a second lumen aperture defined therein the exterior surface of the catheter shaft and in fluid communication with the second lumen, wherein the second lumen aperture is spaced proximally from the first lumen aperture, and
   a distal aperture defined in at least a portion of the distal end portion and in fluid communication with the third lumen, wherein the distal aperture faces distally away from the catheter shaft and is angled proximally away from the distal tip, wherein the distal portion of the catheter is substantially curved in an unstressed state and forms a guard portion having an apex that extends upwardly relative to the single common plane and defines an inner angle measured in the single common plane opposite the apex, wherein the apex is positioned distally of the second lumen aperture.

3. The catheter of claim 2, wherein the catheter shaft is movable in the single common plane between a stressed state and the unstressed state wherein in the stressed state the inner angle is approximately 180 degrees, and the catheter shaft is substantially straight, and wherein in the unstressed state, the inner angle is between about 45 degrees and about 135 degrees.

4. The catheter of claim 2, further comprising a liner, wherein the liner is positioned thereon at least a portion of the inner wall of the third lumen.

5. The catheter of claim 2, wherein the third lumen has a length of between 3 mm and 10 mm.

* * * * *